US005858778A

United States Patent [19]
Alnemri et al.

[11] Patent Number: 5,858,778
[45] Date of Patent: Jan. 12, 1999

[54] SF CASPASE-1 AND COMPOSITIONS FOR MAKING AND METHODS OF USING THE SAME

[75] Inventors: Emad S. Alnemri; Teresa Fernandes-Alnemri, both of Ambler; Gerald Litwack, Bryn Mawr, all of Pa.

[73] Assignee: Thomas Jefferson University, Philadelphia, Pa.

[21] Appl. No.: 773,608

[22] Filed: Dec. 27, 1996

[51] Int. Cl.$^6$ .............................. C12N 9/50; C12N 5/00; C12N 15/00; C07H 21/04

[52] U.S. Cl. ...................... 435/325; 435/219; 435/252.3; 435/252.33; 435/254.11; 435/320.1; 435/348; 536/23.2; 536/24.3; 536/24.31

[58] Field of Search .................................. 435/219, 252.3, 435/252.33, 254.11, 320.1, 325, 348; 536/23.2, 24.3, 24.31

[56] References Cited

U.S. PATENT DOCUMENTS

| 4,736,866 | 4/1988 | Leder et al. | 800/1 |
| 4,873,191 | 10/1989 | Wagner et al. | 435/172.3 |

OTHER PUBLICATIONS

Alnemri, et al., "FKBP46, a Novel Sf9 Insect Cell Nuclear Immunophilin That Forms a Protein–Kinase Complex", *J. Biol. Chem.*, 1994, 269, 30828–30834.

Alnemri, E.S. "Mammalian Cell Death Proteases: A Family of Highly Conserved Aspartate Specific Cysteine Proteases", *J. Cell. Biochem.*, 1997, 64, 33–42.

Beidler, D.R., et al., "The Baculovirus p35 Protein Inhibits Fas and Tumor Necrosis Factor–induced Apoptosis", *J. Biol. Chem.*, 1995, 270, 16526–16528.

Bertin, et al., "Death effector domain–containing herpesvirus and poxvirus proteins inhibit both Fas–and TNFR1–induced apoptosis", *Proc. Natl. Acad. Sci. USA*, 1997, 94, 1172–1176.

Birnbaum, et al., "An Apoptosis–Inhibiting Gene from a Nuclear Polyhedrosis Virus Encoding a polypeptide with Cys–His Sequence Motifs", *J. Virology*, 1994, 68, 2521–2528.

Bump, et al., "Inhibition of ICE Family Proteases by Baculovirus Antiapoptotic Protein p35", *Science*, 1995, 269, 1885–1888.

Clem, et al., "Prevention of Apoptosis by a Baculovirus Gene During Infection of Insect Cells", *Science*, 1991, 254, 1388–1390.

Davies, et al., "Human Papillomavirus Type 16 E7 Associates with a Histone H1 Kinase and with p107 through Sequences Necessary for Transformation", *J. Virology*, 1993, 67, 2521–2528.

Fernandes–Alnemri, et al., "In vitro activation of CPP32 and Mch3 by Mch4, a novel human apoptotic cysteine protease containing two FADD–like domains", *Proc. Natl. Acad. Sci. USA*, 1996, 93, 7464–7469.

Fernandes–Alnemri, et al., "Mch3, a Novel Human Apoptotic Cysteine Protease Highly Related to CPP32[1]", *Cancer Research*, 1995, 55, 6045–6052.

Fernandes–Alnemri, et al., "Mch2, A New Member of the Apoptotic Ced–3/Ice Cysteine Protease Gene Family[1]", *Cancer Research*, 1995, 55, 2737–2742.

Fraser, A. And Evan, G., "A License to Kill", *Cell*, 1996, 85, 781–784.

Henkart, P.A., "ICE Family Proteases: Mediators of All Apoptotic Cell Death?", *Immunity*, 1996, 4, 195–201.

Liston, et al., "Suppression of apoptosis in mammalian cells by NAIP and a related family if IAP genes", *Nature*, 1996, 379, 349–352.

Martin, S.J. and Green, D.R., "Protease Activation during Apoptosis: Death by a Thousand Cuts", *Cell*, 1995, 82, 349–352.

Martinou, et al., "Viral Protein E1B19K and p35 Protect Synpathetic Neurons from Cell Death Induced by NGF Deprivation", *J. Cell Biol.*, 1995, 128, 201–208.

Rabizadeh, et al., "Expression of the Baculovirus p35 Gene Inhibits Mammalian Neural Cell Death", *J. Neurochemistry*, 1993, 61, 2318–2321.

Rothe, et al., "The TNFR2–TRAF Signaling Complex Contains Two Novel Proteins Related to Baculoviral Inhibitor of Apoptosis Proteins", *Cell*, 1995, 83, 1243–1252.

Rotonda, J., et al., "The three–dimensional structure of apopain/CPP32, a key mediator of apoptosis", *Nature Struct. Biol.*, 1996, 3, 619–625.

Srinivasula, S.M., et al., "The Ced–3/Interleukin 1β Converting Enzyme–like Homolog Mch6 and the Lamin–cleaving Enzyme Mch2α Are Substrates for the Apoptotic Mediator CPP32*", *J. Biol. Chem.*, 1996, 271, 27099–27106.

Takahashi, A. And Earnshaw, W.C., "ICE–related proteases in apoptosis", *Curr. Opin. Gen. Dev.*, 1996, 6, 50–55.

Uren, et al., "Cloning and expression of apoptosis inhibitory protein himologs that function to inhibit apoptosis and/or bind tumor necrosis factor receptor–associated factors", *Proc. Natl. Acad. Sci. USA*, 1996, 93, 4974–4978.

Xue, D. And Horvitz, H.R., "Inhibition of the Caenorhabditis elegans cell–death protease CED–3 by a CED–3 cleavage site in baculovirus p35 protein", *Nature*, 1995, 377, 248–251.

(List continued on next page.)

*Primary Examiner*—Robert A. Wax
*Assistant Examiner*—Lisa J. Hobbs
*Attorney, Agent, or Firm*—Woodcock Washburn Kurtz Mackiewicz & Norris LLP

[57] ABSTRACT

A substantially pure protein, Caspase-1, is disclosed. An isolated nucleic acid molecule that comprises a nucleic acid sequence that encodes Caspase-1, is disclosed. An isolated nucleic acid molecule consisting of a nucleic acid sequence that encodes Caspase-1, or a fragment thereof having at least 10 nucleotides is disclosed. Recombinant expression vector comprising a nucleic acid sequence that encodes Caspase-1 and host cells comprising the recombinant expression vector are disclosed. Oligonucleotide molecule comprising a nucleotide sequence complimentary to a nucleic acid sequence that encodes Caspase-1 of at least 5 nucleotides are disclosed. Antibodies that binds to an epitope on Caspase-1 are disclosed. Methods of identifying modulators and substrates of Caspase-1 are disclosed.

13 Claims, 10 Drawing Sheets

OTHER PUBLICATIONS

Marra et al. (1997) rs10h06.r1 Sommer *Pristionchus pacificus* cDNA clone 1242 5' similar to SW: CYB_CAEEL p24890 Cytochrome B, EST Database Accession No. AA192072.

Chakrabarti et al. (1994) Analysis of Expressed Sequence Tags from *Plasmodium falciparum*. Mol. Biochem. Parasitol. 66: 97–104.

Chakrabarti et al. (1994) 0671c3 *Plasmodium falciparum* cDNA clone 0671c 5', EST Database Accession No. T18120.

FIGURE 1A

```
                                    p19/p18
  1  MLDGKQDNGN VDSVDIKQRT NGGGDEGDAL GSNSSSQPNR VARMPVDRNA   50
 51  PYYNMNHKHR GMAIIFNHEH FDIHSLKSRT GTNVDSDNLS KVLKTLGFKV  100
101  TVFPNLKSEE INKFIQQTAE MDHSDADCLL VAVLTHGELG MLYAKDTHYK  150
                                                     p12
151  PDNLWYYFTA DKCPTLAGKP KLFFI QACQG DRLDGGITLS RTETDGSPST  200
                                  ↑         ↑         ↑
201  SYRIPVHADF LIAFSTVPGY FSWRNTTRGS WFMQALCEEL RYAGTERDIL  250
251  TLLTFVCQKV ALDFESNAPD SAMMHQQKQV PCITSMLTRL LVFGKKQSH*  299
```

FIGURE 1B

|   |         |     | Large Subunit |         |         |         | Small Subunit |
|---|---------|-----|---------------|---------|---------|---------|---------------|
| I | Sf Casp-1 | 77  | KSRTGT..LTHGEL..FIQACQG.....DRLDG..TETDG..GYFSWRNTTRGSWFM |
|   | Mch6    | 178 | RTRTGS..LSHGCQ..FIQACGGEQ..PEPDA..DQLDA..GFVSWRDPKSGSWYV |
|   | Mch5    | 275 | RDRNGT..LSHGDK..FIQACQGDN..VETDS..LEMDL..NCVSYRNPAEGTWYI |
|   | Mch4    | 255 | KDRQGT..LTHGRF..FIQACQGEE..IEADA........GYVSFRHVEEGSWYI |
|   | Mch3    | 85  | GVRNGT..LSHGEE..FIQACRGTE..IQADS........GYYSWRSPGRGSWFV |
|   | Mch2    | 62  | PERRGT..LSHGEG..IIQACRGNQ..DVVDN..TEVDA..GYYSHERETVNGSWYI |
|   | CPP32   | 62  | TSRSGT..LSHGEE..IIQACRGTE..IETDS........GYISWRNSKDGSWFI |
|   | CED-3   | 257 | PTRNGT..LSHGEE..FVQACRGER..DSVDG........QYVSWRNSARGSWFI |
| II | ICE    | 177 | PRRTGA..MSHGIR..IIQACRGDS..WFKDS..FEDDA..DNVSWRHPTMGSVFI |
|   | TX      | 150 | PPRNGA..MSHGIL..IVQACRGAN..WVKDS..LEEDA..HNVSWRDSTMGSIFI |
|   | ICErelIII | 191 | PARNGA..MSHGIL..IVQACRGEK..WVRDS..LEADS..HNVSWRDRTRGSIFI |
| III | ICH-1 | 200 | EFRSGG..LSHGVE..FIQACRGDE..DQQDG..EESDA..GTAAMRNTKRGSWYI |
|   |         |     | b    acc    bac    DX    DX    aabaa a ba |

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2658 base pairs
        ( B ) TYPE: nucleic acid
        ( C ) STRANDEDNESS: double
        ( D ) TOPOLOGY: Not Relevant ( i i ) MOLECULE TYPE: cDNA ( i x ) FEATURE:
        ( A ) NAME/KEY: CDS
        ( B ) LOCATION: 140..1039

( x i ) SEQUENCE DESCRIPTION: SEQ ID NO:1:

```
GGAATTCGGC  ACGAGGCGCA  ATAAGTTTTT  CGGTGAATTT  GGTGATCGTA  TATTGGCGTA         60

CAGTTGATAA  AAGTTTACTG  TTAAATAAAT  AAAATCTTAT  TTTATTTAAC  TCAATCGTCA        120

AAAGTATAGA  ACTATCAAA  ATG CTG GAC GGA AAA CAA GAC AAT GGA AAT GTG           172
                      Met Leu Asp Gly Lys Gln Asp Asn Gly Asn Val
                        1               5                  10

GAT AGT GTT GAT ATC AAA CAA AGA ACC AAT GGT GGT GGC GAT GAA GGC              220
Asp Ser Val Asp Ile Lys Gln Arg Thr Asn Gly Gly Gly Asp Glu Gly
         15                  20                  25
```

-continued

| | | | | | | | | | | | | | | | | |
|---|---|---|---|---|---|---|---|---|---|---|---|---|---|---|---|---|
| GAC | GCT | CTG | GGC | AGT | AAC | AGT | TCT | TCG | CAA | CCC | AAC | CGT | GTC | GCT | AGG | 268 |
| Asp | Ala | Leu | Gly | Ser | Asn | Ser | Ser | Ser | Gln | Pro | Asn | Arg | Val | Ala | Arg | |
| | | | 30 | | | | 35 | | | | | 40 | | | | |
| ATG | CCA | GTT | GAT | AGA | AAT | GCC | CCT | TAT | TAC | AAC | ATG | AAC | CAT | AAA | CAT | 316 |
| Met | Pro | Val | Asp | Arg | Asn | Ala | Pro | Tyr | Tyr | Asn | Met | Asn | His | Lys | His | |
| | | | 45 | | | | | 50 | | | | | 55 | | | |
| CGT | GGT | ATG | GCC | ATT | ATT | TTC | AAC | CAC | GAG | CAT | TTC | GAC | ATT | CAC | AGC | 364 |
| Arg | Gly | Met | Ala | Ile | Ile | Phe | Asn | His | Glu | His | Phe | Asp | Ile | His | Ser | |
| 60 | | | | | 65 | | | | | 70 | | | | | 75 | |
| CTG | AAG | TCC | CGT | ACT | GGC | ACG | AAT | GTA | GAC | AGC | GAC | AAC | CTT | TCC | AAA | 412 |
| Leu | Lys | Ser | Arg | Thr | Gly | Thr | Asn | Val | Asp | Ser | Asp | Asn | Leu | Ser | Lys | |
| | | | | 80 | | | | | 85 | | | | | 90 | | |
| GTT | CTT | AAA | ACC | TTG | GGA | TTC | AAA | GTT | ACG | GTG | TTC | CCT | AAC | TTA | AAA | 460 |
| Val | Leu | Lys | Thr | Leu | Gly | Phe | Lys | Val | Thr | Val | Phe | Pro | Asn | Leu | Lys | |
| | | | | 95 | | | | | 100 | | | | | 105 | | |
| TCA | GAA | GAA | ATC | AAT | AAA | TTT | ATC | CAG | CAG | ACT | GCA | GAG | ATG | GAC | CAT | 508 |
| Ser | Glu | Glu | Ile | Asn | Lys | Phe | Ile | Gln | Gln | Thr | Ala | Glu | Met | Asp | His | |
| | | 110 | | | | | 115 | | | | | 120 | | | | |
| TCA | GAC | GCT | GAC | TGT | TTA | CTT | GTT | GCC | GTT | TTA | ACC | CAT | GGA | GAG | CTA | 556 |
| Ser | Asp | Ala | Asp | Cys | Leu | Leu | Val | Ala | Val | Leu | Thr | His | Gly | Glu | Leu | |
| | 125 | | | | | 130 | | | | | 135 | | | | | |
| GGA | ATG | CTG | TAT | GCC | AAA | GAT | ACT | CAT | TAC | AAG | CCA | GAC | AAC | CTG | TGG | 604 |
| Gly | Met | Leu | Tyr | Ala | Lys | Asp | Thr | His | Tyr | Lys | Pro | Asp | Asn | Leu | Trp | |
| 140 | | | | | 145 | | | | | 150 | | | | | 155 | |
| TAC | TAC | TTT | ACT | GCT | GAC | AAA | TGC | CCC | ACA | CTG | GCT | GGA | AAA | CCT | AAG | 652 |
| Tyr | Tyr | Phe | Thr | Ala | Asp | Lys | Cys | Pro | Thr | Leu | Ala | Gly | Lys | Pro | Lys | |
| | | | | 160 | | | | | 165 | | | | | 170 | | |
| CTC | TTC | TTT | ATT | CAG | GCT | TGC | CAA | GGT | GAC | AGA | TTG | GAT | GGT | GGT | ATT | 700 |
| Leu | Phe | Phe | Ile | Gln | Ala | Cys | Gln | Gly | Asp | Arg | Leu | Asp | Gly | Gly | Ile | |
| | | | 175 | | | | | 180 | | | | | 185 | | | |
| ACT | CTG | AGC | CGC | ACT | GAG | ACA | GAT | GGC | TCA | CCT | TCT | ACT | TCG | TAT | AGG | 748 |
| Thr | Leu | Ser | Arg | Thr | Glu | Thr | Asp | Gly | Ser | Pro | Ser | Thr | Ser | Tyr | Arg | |
| | | 190 | | | | | 195 | | | | | 200 | | | | |
| ATT | CCC | GTA | CAT | GCT | GAT | TTC | TTG | ATT | GCA | TTT | TCA | ACT | GTA | CCT | GGA | 796 |
| Ile | Pro | Val | His | Ala | Asp | Phe | Leu | Ile | Ala | Phe | Ser | Thr | Val | Pro | Gly | |
| | 205 | | | | | 210 | | | | | 215 | | | | | |
| TAC | TTT | TCT | TGG | AGG | AAC | ACT | ACC | AGA | GGT | TCA | TGG | TTT | ATG | CAA | GCT | 844 |
| Tyr | Phe | Ser | Trp | Arg | Asn | Thr | Thr | Arg | Gly | Ser | Trp | Phe | Met | Gln | Ala | |
| 220 | | | | | 225 | | | | | 230 | | | | | 235 | |
| TTG | TGT | GAA | GAG | CTA | CGC | TAT | GCA | GGA | ACA | GAG | AGG | GAC | ATT | CTG | ACA | 892 |
| Leu | Cys | Glu | Glu | Leu | Arg | Tyr | Ala | Gly | Thr | Glu | Arg | Asp | Ile | Leu | Thr | |
| | | | | 240 | | | | | 245 | | | | | 250 | | |
| TTG | CTG | ACT | TTT | GTG | TGT | CAG | AAG | GTT | GCG | CTA | GAC | TTT | GAG | TCT | AAT | 940 |
| Leu | Leu | Thr | Phe | Val | Cys | Gln | Lys | Val | Ala | Leu | Asp | Phe | Glu | Ser | Asn | |
| | | | 255 | | | | | 260 | | | | | 265 | | | |
| GCC | CCT | GAC | TCA | GCG | ATG | ATG | CAT | CAA | CAG | AAA | CAA | GTT | CCC | TGC | ATC | 988 |
| Ala | Pro | Asp | Ser | Ala | Met | Met | His | Gln | Gln | Lys | Gln | Val | Pro | Cys | Ile | |
| | | 270 | | | | | 275 | | | | | 280 | | | | |
| ACC | AGC | ATG | CTC | ACA | CGT | CTG | CTT | GTG | TTT | GGT | AAG | AAG | CAG | TCC | CAC | 1036 |
| Thr | Ser | Met | Leu | Thr | Arg | Leu | Leu | Val | Phe | Gly | Lys | Lys | Gln | Ser | His | |
| 285 | | | | | 290 | | | | | 295 | | | | | | |
| TGA | TATACCGTGT | TGTTGTGCTG | TACCTATGTT | AGGTATCCAA | ATCTCATTAG | | | | | | | | | | | 1089 |
| * | | | | | | | | | | | | | | | | |
| 300 | | | | | | | | | | | | | | | | |

CTCTACTTAT ACAAATATAA TAAGGAAGGC TACTGTTCCT TCTTGTCTAA ATTAGATAAT       1149

AATGTTCAAT GGCTGTTCAA AATGTTTTAA TGTTAAATGC ATTTTAACTT TTACTTTTTG       1209

AGATTAATTT TGGTTCTGCA TTTTTTTTAA GTGACTCATA GTTTTTGGT GTCCAAATGT        1269

AATAATGGTG GTTGTTAGAT GTAAATTGTA TTGCCATGTC ACAAATTATG TAAGTAGTAG       1329

```
TACTTACATA  TTATGTGCCA  GTGATAATAA  GTTAGATAA   TTAGAAAAAA  TGTATTTTAT   1389

GCTCATTTTC  ATAGTTAATA  ATGAGTGCAC  AAACTTTAAA  ATTATATTTC  ATAATATTAT   1449

GTATTTGCTC  AAATAAAGTA  TAAAAGGAAA  TACACTCCCA  GCCATGTTTG  AAAATTATTC   1509

CAAGTTTTAA  TACAAAAACA  TTTGAGATTA  TATTTCTAAA  GTACTTAATA  ATAAATAATA   1569

AATAATTTAT  AATCATGAAG  TGAATGAAAG  AACAGACTGA  TGAACATGAA  CAAAGGAATC   1629

AATTTCTATA  GCAACTGTAC  ATATCATAAA  TGTCAAACAC  CTTTTATGTT  TCTCTTAGGA   1689

TAAACTTGTG  TTGTAATAAC  TTATAAATTT  AATGAGCTAT  TTAAAGGTCT  GATATCAACA   1749

GTGTTACCTA  TTTTTGTTAT  GTTTTATTTT  TTTGCATTAT  TCAAAACTGT  AGGCAGACCA   1809

CCTTTGTTAA  GACATTTATT  TTTAATAAGA  GCATTTATTG  TTGTATTAGT  TGTTAGTAGC   1869

ACCATAACAT  TTCCTGCCAA  TTTTACACTT  AGTACCTACC  TGTTTTCTTT  TAATTTTTTT   1929

GTAAACTGGC  TTGAATGAAA  ATGTCTAGTA  TTGCATGCCC  ATGTGTCATA  ATAAAAGTTT   1989

TAATTATAAT  ATGTTTAATT  ATCAGTAATG  CATTATATTA  TATAAGTATT  GTAATAATAA   2049

AACTTGAATA  TAAAATTTTG  GATTCAGGTA  TGTGATAATG  GCATCAATTG  ACTGATTTAA   2109

CTTTAGTGTG  AATAAAGTAT  CTGTGAGAAC  TAAATTGCCA  TGGATTTATA  TTAGAAATAA   2169

TATTTTAGTT  ATCAATATAT  TAAAATTGTG  CCTTGTCCAA  CTGTAAAAGT  ATTGTAGAAA   2229

CTGTGAAGTG  AATACAAAGA  GGAGATGTTA  TATGTATAAC  TGGATTTTCT  TTTAACATAA   2289

TGCTTGACAC  TACGGGGAGC  GCGGGACGTT  ACAAACCACA  CCCTCTCTAT  TTTAAACATG   2349

CAGTTCCATA  CTACAATTAT  GTTGCCAATT  GTCCACATTT  TAATGTGCTT  GTTTCTGAAT   2409

GGTTAGAACC  TATCTACACC  TTTTTACTTT  AATATCATTG  GGCAGGGCCC  ATTTATTTTG   2469

TCACAGCGCA  CAATTACATT  ATGGCATCTC  CTCTGTACCT  ATTTCATGGT  TGAAACACAG   2529

CTAAATGATG  GATCTTATTA  GTACTCTAGC  TCTTCCCATA  GACTTTGAT   GCAATGATAT   2589

GAGTGGTTTG  TATTTTTTAT  AATAAATGCT  TATATACAGT  AAACTTAAAG  CAATAAATTC   2649

TTCCATTCT                                                                2658
```

( 2 ) INFORMATION FOR SEQ ID NO:2:

( i ) SEQUENCE CHARACTERISTICS:
        ( A ) LENGTH: 299 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Asp  Gly  Lys  Gln  Asp  Asn  Gly  Asn  Val  Asp  Ser  Val  Asp  Ile
 1                    5                   10                       15

Lys  Gln  Arg  Thr  Asn  Gly  Gly  Gly  Asp  Glu  Gly  Asp  Ala  Leu  Gly  Ser
                20                   25                       30

Asn  Ser  Ser  Ser  Gln  Pro  Asn  Arg  Val  Ala  Arg  Met  Pro  Val  Asp  Arg
           35                   40                       45

Asn  Ala  Pro  Tyr  Tyr  Asn  Met  Asn  His  Lys  His  Arg  Gly  Met  Ala  Ile
      50                        55                   60

Ile  Phe  Asn  His  Glu  His  Phe  Asp  Ile  His  Ser  Leu  Lys  Ser  Arg  Thr
 65                        70                   75                        80

Gly  Thr  Asn  Val  Asp  Ser  Asp  Asn  Leu  Ser  Lys  Val  Leu  Lys  Thr  Leu
                     85                   90                        95

Gly  Phe  Lys  Val  Thr  Val  Phe  Pro  Asn  Leu  Lys  Ser  Glu  Glu  Ile  Asn
               100                       105                      110
```

| | | | | | | | | | | | | | | |
|---|---|---|---|---|---|---|---|---|---|---|---|---|---|---|
| Lys | Phe | Ile 115 | Gln | Gln | Thr | Ala | Glu 120 | Met | Asp | His | Ser | Asp 125 | Ala | Asp | Cys |
| Leu | Leu 130 | Val | Ala | Val | Leu | Thr 135 | His | Gly | Glu | Leu | Gly 140 | Met | Leu | Tyr | Ala |
| Lys 145 | Asp | Thr | His | Tyr | Lys 150 | Pro | Asp | Asn | Leu | Trp | Tyr 155 | Tyr | Phe | Thr | Ala 160 |
| Asp | Lys | Cys | Pro | Thr 165 | Leu | Ala | Gly | Lys | Pro 170 | Lys | Leu | Phe | Phe | Ile 175 | Gln |
| Ala | Cys | Gln | Gly 180 | Asp | Arg | Leu | Asp | Gly 185 | Gly | Ile | Thr | Leu | Ser 190 | Arg | Thr |
| Glu | Thr | Asp 195 | Gly | Ser | Pro | Ser | Thr 200 | Ser | Tyr | Arg | Ile | Pro 205 | Val | His | Ala |
| Asp | Phe 210 | Leu | Ile | Ala | Phe | Ser 215 | Thr | Val | Pro | Gly | Tyr 220 | Phe | Ser | Trp | Arg |
| Asn 225 | Thr | Thr | Arg | Gly | Ser 230 | Trp | Phe | Met | Gln | Ala 235 | Leu | Cys | Glu | Glu | Leu 240 |
| Arg | Tyr | Ala | Gly | Thr 245 | Glu | Arg | Asp | Ile | Leu 250 | Thr | Leu | Leu | Thr | Phe 255 | Val |
| Cys | Gln | Lys | Val 260 | Ala | Leu | Asp | Phe | Glu 265 | Ser | Asn | Ala | Pro | Asp 270 | Ser | Ala |
| Met | Met | His 275 | Gln | Gln | Lys | Gln | Val 280 | Pro | Cys | Ile | Thr | Ser 285 | Met | Leu | Thr |
| Arg | Leu 290 | Leu | Val | Phe | Gly | Lys 295 | Lys | Gln | Ser | His | * 300 | | | | |

SF CASPASE-1 AND COMPOSITIONS FOR MAKING AND METHODS OF USING THE SAME

ACKNOWLEDGMENT OF GOVERNMENT RIGHTS

This invention was made with Government support under Research Grants AG 13481 and AI 35035 from the National Institutes of Health. The Government has certain rights in this invention.

FIELD OF THE INVENTION

The invention relates to the identification and cloning of Caspase-1, a novel Sf9 insect cell nuclear immunophilin that forms a protein kinase complex, and to methods of making and using the same.

BACKGROUND OF THE INVENTION

Aspartate-specific cysteine proteases (ASCPs) play a central and evolutionarily conserved role in transducing the apoptotic signal and final execution of apoptosis (Martin, S. J. et al., Cell 1995, 82, 349–352; Henkart, P. A., Immunity 1996, 4, 195–201; Takahashi, A. et al., Curr. Opin. Gen. Dev. 1996, 6, 50–55; Fraser, A. et al., Cell 1996, 85, 781–784; and Alnemri, E. S., J. Cell. Biochem. 1996, 62, In Press). In the human there are ten different ASCPs, divided into three subfamilies based on their homology to the mammalian proinflammatory prototype interleukin 1-beta converting enzyme (ICE) and the nematode proapoptotic prototype CED-3 (Fernandes-Alnemri T. et al., Proc. Natl. Acad. Sci. 1996, 93, 7464–7469; and Srinivasula, S. M., et al., J. Biol. Chem. 1996, 271, In Press). In mammalian cells it is now believed that the two ASCPs, Mch4 and Mch5 (MACH/FLICE), which contain two FADD-like domains in their long N-terminal prodomain might be the most upstream transducers of diverse apoptotic signals, whereas CPP32, Mch2, and Mch3 which have short prodomains are the downstream executioners of apoptosis (Fernandes-Alnemri, T. et al., Supra; Srinivasula, S. M., et al., Supra; Boldin, M. P. et al., Cell 1996, 85, 803–815; and Muzio, M. et al., Cell 1996, 85, 817–827).

Studies with the baculovirus Autographa californica and its insect host S. frugiperda identified baculovirus encoded proteins, p35 and IAPs, that suppress baculovirus-induced apoptosis in S. frugiperda cells (Clem, R. J. et al., Science 1991, 254, 1388–1390; Crook, N. E. et al., J. Virol. 1993, 67, 2521–2528; and Birnbaum, M. J. et al., J. Virol. 1994, 68, 2521–2528). These proteins are expressed by the baculovirus to counter the host's antiviral defense (i.e., apoptosis) to ensure virus latency and multiplication. Mammalian anti-apoptotic proteins homologous to baculovirus IAPs have recently been identified (Rothe, M. et al., Cell 1995, 83, 1243–1252; Liston, P. et al., Nature 1996, 379, 349–353; and Uren, A. G. et al., Proc. Natl. Acad. Sci. USA 1996, 93, 4974–4978). In contrast, no mammalian counterpart of p35 has yet been identified. Nevertheless, p35 is an effective suppressor of apoptosis in mammalian cells (Rabizadeh, S. et al., J. Neurochem. 1994, 61(6), 2318–2321; Martinou, I. et al., J. Cell Biol. 1995, 128, 201–208; and Beidler, D. R. et al., J. Biol. Chem. 1995, 270, 16526–16528). Its anti-apoptotic activity is attributed to its ability to interact with and potently inhibit members of the ASCP family (Bump, N. J. et al., Science 1995, 269, 1885–1888; and Xue, D et al., Nature 1995, 377, 248–251). This suggests that the apoptotic program in S. frugiperda is similar to the mammalian program and is mediated by active ASCP(s). This is further supported by the recent observation that baculovirus infection of S. frugiperda cells activate an ASCP that can cleave p35 (Bertin, J. et al., J. Virol. 1996, 70, 6251–6259).

There is a need to identify and clone the S. frugiperda ASCP that is responsible for execution of apoptosis in this organism. There is a need to identify proteases, particularly those involved in apoptosis. There is a need to identify compounds that inhibit proteases. There is a need to identify compounds that enhance the activity of proteases. There is a need to study and understand the mechanisms by which apoptosis is initiated, proceeds and is inhibited, and for reagents useful in such studies. There remains a need to identify new protease inhibitors and drugs for preventing or initiating apoptosis. There is a need for kits and methods of identifying such compounds. There remains a need to identify new protease activity enhancers and drugs for preventing or initiating apoptosis. There is a need for kits and methods of identifying such compounds. There is a need for isolated proteases and for compositions and methods of producing and isolating proteases. There is a need to isolated proteins that are proteases. There is a need to isolated nucleic acid molecules that encode proteases.

SUMMARY OF THE INVENTION

The invention relates to substantially pure proteins that have amino acid sequences shown in SEQ ID NO:2.

The invention relates to isolated nucleic acid molecules that comprise nucleic acid sequences that encode a protein that has an amino acid sequence shown in SEQ ID NO:2.

The invention relates to isolated nucleic acid molecules that consist of SEQ ID NO:1 or a fragment thereof having at least 5 nucleotides.

The invention relates to a recombinant expression vector comprising the nucleic acid molecule that has a nucleotide sequence that comprises SEQ ID NO:1.

The invention relates to a host cell comprising a recombinant expression vector comprising the nucleic acid molecule that has a nucleotide sequence that comprises SEQ ID NO:1.

The invention relates to an oligonucleotide molecule comprising a nucleotide sequence complimentary to a nucleotide sequence of at least 5 nucleotides of SEQ ID NO:1.

The invention relates to isolated antibodies that bind to an epitope on SEQ ID NO:2.

The invention relates to methods of identifying compounds that are processed by Caspase-1.

BRIEF DESCRIPTION OF THE FIGURES

FIGS. 1A and 1B show the amino acid sequence of Sf proCaspase-1 and its homology to other ASCPs.

DETAILED DESCRIPTION OF THE INVENTION

Figure 2A:
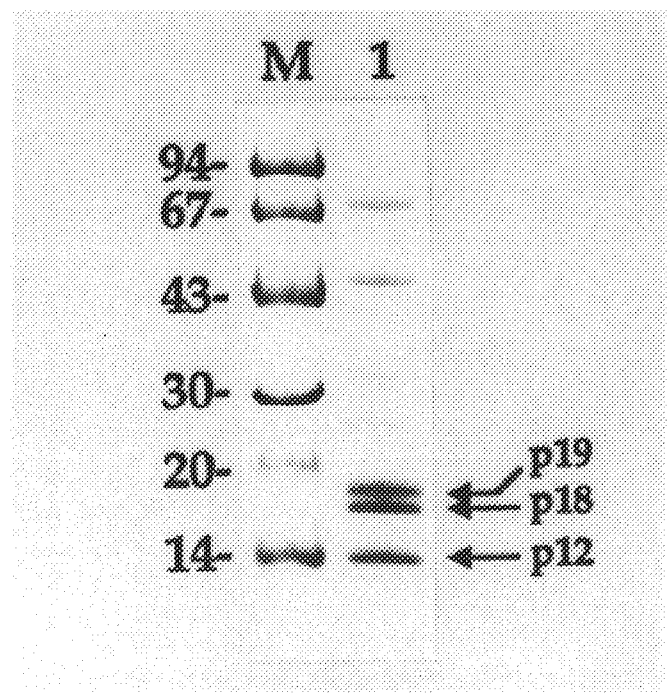
FIGS. 2A, 2B and 2C show data from experiments evaluating subunit structure of mature Sf Caspase-1.

The discovery of Caspase-1 provides the means to study the process of apoptosis and to identify and study the activity of compounds that are involved in that process.

According to the present invention, Caspase-1 may be used to screen compounds to identify those compounds that are processed by it as well as those compounds that inhibit or enhance its activity. Methods and kits are provided for screening compounds which can inhibit or enhance Caspase-1 activity which can be used to inhibit or enhance, respectively, the apoptosis program. Reagents useful in the method and kits as well as reagents for producing such reagents are provided.

In addition, isolated Caspase-1 may be used to identify protease substrates. Isolated Caspase-1 protein may be used in affinity chromatography columns and protocols to identify proteins such as cellular proteins which are processed by it. Examples of such proteins include FKBP46 and p35.

The nucleotide and amino acid sequences that encode Caspase-1, which are disclosed herein, allow for the production of pure protein, the design of probes which specifically hybridize to nucleic acid molecules that encode Caspase-1, and the design and production of nucleic acid molecules, recombinant vectors and host cells to produce Caspase-1 protein. In addition, antisense compounds that inhibit transcription of Caspase-1 and anti-Caspase-1 antibodies are provided. Anti-Caspase-1 antibodies may inhibit Caspase-1 activity. The antibodies may also be used in methods of isolating pure Caspase-1.

The present invention provides substantially purified Caspase-1 which has amino acid sequences consisting of SEQ ID NO:2. Caspase-1 can be isolated from natural sources, produced by recombinant DNA methods or synthesized by standard protein synthesis techniques.

Antibodies which specifically bind to Caspase-1 may be used to purify the protein from natural sources using well known techniques and readily available starting materials. Such antibodies may also be used to purify Caspase-1 from material present when producing the protein by recombinant DNA methodology. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. Antibodies that bind to an epitope which is present on Caspase-1 are useful to isolate and purify Caspase-1 from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual,* Cold Spring Harbor Laboratory, Cold Spring Harbor, N.Y. which is incorporated herein by reference. Briefly, for example, Caspase-1 or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to Caspase-1 the hybridoma which produces them is cultured to produce a continuous supply of antibodies.

According to some embodiments of the present invention relates, an isolated nucleic acid molecule comprising a nucleotide sequence that encodes Caspase-1 that comprises the amino acid sequence of SEQ ID NO:2 is provided. Such molecules can be routinely designed using the information set forth in SEQ ID NO:2.

Using standard techniques and readily available starting materials, a nucleic acid molecule that encodes Caspase-1 may be isolated from a cDNA library, using probes or primers which are designed using the nucleotide sequence information disclosed in SEQ ID NO:1. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolate nucleic acid molecules of the invention are useful to prepare constructs and recombinant expression systems for preparing Caspase-1.

A cDNA library may be generated by well known techniques. A cDNA clone which contains one of the nucleotide sequences set out is identified using probes that comprise at least a portion of the nucleotide sequence disclosed in SEQ ID NO:1. The probes have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1, PCR primers for amplifying genes and cDNA having SEQ ID NO:1, and antisense molecules for inhibiting transcription and translation of genes and cDNA, respectively, which encode Caspase-1 having the amino acid sequence of SEQ ID NO:2.

The cDNA that encodes Caspase-1 may be used as a molecular marker in electrophoresis assays in which cDNA from a sample is separated on an electrophoresis gel and Caspase-1 probes are used to identify bands which hybridize to such probes. Specifically, SEQ ID NO:1 or portions thereof, may be used as a molecular marker in electrophoresis assays in which cDNA from a sample is separated on an electrophoresis gel and Caspase-1 specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes Caspase-1. Electrophoresis gels useful in such an assay include standard polyacrylamide gels as described in Sambrook et al., *Molecular Cloning a Laboratory Manual,* Second Ed. Cold Spring Harbor Press (1989) which is incorporated herein by reference.

The nucleotide sequences in SEQ ID NO:1 may be used to design probes, primers and complimentary molecules which specifically hybridize to the unique nucleotide sequences of Caspase-1. Probes, primers and complimentary molecules which specifically hybridize to nucleotide sequence that encodes Caspase-1 may be designed routinely by those having ordinary skill in the art. As used herein, the term "specifically hybridize to nucleotide sequence that encodes Caspase-1" is meant to refer to nucleic acid molecules which unique nucleotide sequences that hybridize to Caspase-1 encoding sequences but not other known protein encoding sequences, such as sequences identical to portions of SEQ ID NO:1. This, the unique sequences described herein are those that do not overlap with known sequences.

The present invention also includes labeled oligonucleotides which are useful as probes for performing oligonucleotide hybridization methods to identify Caspase-1. The oligonucleotides include sequences that specifically hybridize to nucleotide sequences that encode Caspase-1. Accordingly, the present invention includes probes that can be labeled and hybridized to unique nucleotide sequences that encode Caspase-1. The labeled probes of the present invention are labeled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of Caspase-1.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length. PCR primers include at least one primer which includes a nucleotide sequence that specifically hybridizes to nucleotide sequence that encodes Caspase-1.

One having ordinary skill in the art can isolate the nucleic acid molecule that encode Caspase-1 and insert it into an expression vector using standard techniques and readily available starting materials.

The present invention relates to a recombinant expression vector that comprises a nucleotide sequence that encodes Caspase-1 that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the Caspase-1 of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing Caspase-1.

The present invention relates to a host cell that comprises the recombinant expression vector that includes a nucleotide sequence that encodes Caspase-1 that comprises SEQ ID NO:1. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli,* yeast cells such as *S. cerevisiae,* insect cells such as *S. frugiperda,* non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes Caspase-1 that comprises the amino acid sequence of SEQ ID NO:2. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes Caspase-1 is operably linked to a mammary cell specific promoter whereby the coding sequence is only expressed in mammary cells and the recombinant protein so expressed is recovered from the animal's milk. In some embodiments, the coding sequence that encodes Caspase-1 is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli.* The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce Caspase-1 using routine techniques and readily available starting materials. (See e.g., Sambrook et al., *Molecular Cloning a Laboratory Manual,* Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences,. such as promoters and polyadenylation signals, and preferably enhancers, are readily available and known in the art for a variety of hosts. See e.g., Sambrook et al., *Molecular Cloning a Laboratory Manual,* Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes the Caspase-1 is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate Caspase-1 that is produced using such expression systems. The methods of purifying Caspase-1 from natural sources using antibodies which specifically bind to Caspase-1 as described above, may be equally applied to purifying Caspase-1 produced by recombinant DNA methodology.

Examples of genetic constructs include Caspase-1 coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes Caspase-1 from readily available starting materials. Such gene constructs are useful for the production of Caspase-1.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce Caspase-1. Preferred animals are rodents, particularly rats and mice, and goats.

In addition to producing these proteins by recombinant techniques, automated peptide synthesizers may also be employed to produce Caspase-1. Such techniques are well known to those having ordinary skill in the art and are useful if derivatives which have substitutions not provided for in DNA-encoded protein production.

According to one aspect of the invention, compounds may be screened to identify compounds that inhibit or enhance Caspase-1 activity. Substrates of Caspase-1 include baculovirus protein p35 and the Sf immunophillin FKBP46. Assays may be performed combining Caspase-1 with a substrate in the presence or absence of a test compound. The level of Caspase-1 activity in the presence of the test compound is compared to the level in the absence of the test compound. If Caspase-1 activity is increased by the presence of the test compound, the test compound is an enhancer. Caspase-1 activity is decreased by the presence of the test compound, the test compound is an inhibitor. In some embodiments of the invention, the preferred concentration of test compound is between 1 $\mu$M and 500$\mu$M. A preferred concentration is 10 $\mu$M to 100 $\mu$M. In some preferred embodiments, it is desirable to use a series of dilutions of test compounds.

Kits are included which comprise containers with reagents necessary to screen test compounds. Such kits include a container with Caspase-1 protein, a container with a substrate such as FKBP46 or p35, which is preferably a labeled substrate, and instructions for performing the assay. Kits may include a control inhibitor such as anti-Caspase-1 neutralizing antibodies.

Combinatorial libraries may be screened to identify compounds that enhance or inhibit Caspase-1 activity.

EXAMPLE

To identify and clone the *S. frugiperda* ASCP that is responsible for execution of apoptosis in this organism, we employed a degenerate PCR approach designed to identify ASCPs in different species. Here we report the complete amino acid sequence of an *S. frugiperda* ASCP named Sf Caspase-1, as deduced from its cDNA. We demonstrate that this protease is capable of cleaving p35 and is potently inhibited by p35. This protease is also able to induce apoptosis in Sf9 cells and cleave the Sf9 nuclear immunophilin FKBP46. Sf Caspase-1 has a short prodomain and is highly related to human CPP32 and Mch3, implying that it is a downstream executioner of apoptosis.

MATERIALS AND METHODS

Cloning of Sf Caspase-1 proenzyme: To clone Sf Caspase-1 proenzyme, a 10 $\mu$l aliquot of Sf9 λ Uni-ZAP™

XR cDNA library (Alnemri, E. S. et al., *J. Biol. Chem.* 1994, 269, 30828–30834, which is incorporated herein by reference) containing ~10⁸ pfu was denatured at 99° C. for 5 min and used as a template for PCR amplification with a degenerate primer encoding the pentapeptide GSWFI/GSWYI and T3 vector-specific primer (Stratagene) as described previously (Fernandes-Alnemri, T. et al., *Cancer Res.* 1995, 55, 2737–2742, which is incorporated herein by reference). Secondary amplification products were obtained with a degenerate primer encoding QACRG and the SK-Zap primer (Fernandes-Alnemri, T. et al., *Cancer Res.* 1995, 55, 2737–2742) and then cloned into a Sma I cut pBluescript II KS⁺ vector. The partial cDNA was sequenced, excised from the vector, radiolabeled and used to screen the original Sf9 cDNA library. Positive λ clones were purified, rescued into the pBluescript II SK³¹ plasmid vector and sequenced.

Expression of Sf proCaspase-1 in Bacteria and Assay of Enzyme Activity: The open reading frame of Sf proCaspase-1 was subcloned into the bacterial expression vector pET21b in-frame with an N-terminal T7-tag and a C-terminal His-tag (pET21b-SfCasp-1). The protein was expressed in BL21(DE3) bacteria and assayed as described in Fernandes-Alnemri, T. et al., *Cancer Res.* 1995, 55, 2737–2742 and Fernandes-Alnemri, T. et al., *Cancer Res.* 1995, 55, 6045–6052, which are incorporated herein by reference. The recombinant protease was purified on a Ni⁺²-affinity resin and used for microsequencing and the gel cleavage assays as described below. ProCPP32 and proMch3 were expressed and purified in a similar fashion.

Bacterial expression and purification of p35 and CrmA: The open reading frame of baculovirus p35 was subcloned in the bacterial expression vector pET21b in-frame with a C-terminal His-tag but without an N-terminal T7-tag. The p35-His6 recombinant protein was purified on a Ni⁺²-affinity resin and used in the inhibition studies. CrmA was expressed as a GST-CrmA fusion protein in *E. coli*, purified on glutathione-Sepharose and then used in the inhibition studies.

Construction of recombinant Sf proCaspase-1 baculovirus: A proenzyme of Sf Caspase-1 with an N-terminal T7-tag and a C-terminal His6-tag was generated by PCR using the pET21b-SfCasp-1 as a template and then subcloned in the baculovirus transfer vector pVL1393 under the polyhedrin promoter. The recombinant baculovirus was produced as previously described in Alnemri, E. S. et al., *J. Biol. Chem.* 1994, 269, 30828–30834.

Preparation of Sf9 apoptotic extracts: Sf9 cells were infected with wild type or a p35 null mutant baculovirus (vp35Δ baculovirus, generously provided by Dr. Lois Miller, University of Georgia, Athens, Ga.) and harvested 24 h after infection. The cells were suspended in ICE-buffer and lysed by 2–3 cycle of freeze-thaw followed by homogenization. The cell lysates were centrifuged at 16000 g for 15 min and the supernatants were collected and then used for the enzymatic assays.

In vitro Transcription/Translation and Cleavage Assays: p35 and SF-Caspase-1 cDNAs were in vitro transcribed and translated in the presence of [³⁵S]methionine using Promega's coupled transcription/translation TNT kit according to the manufacturer's recommendations. Two microliters of the translation reactions were incubated with purified enzymes in ICE-buffer (25 mM HEPES, 1 mM EDTA, 5 mM DTT, 0.1% CHAPS, pH 7.5), in a final volume of 10 μl. The reaction was incubated at 37° C. for various times and then analyzed by Tricine-SDS-PAGE and autoradiography.

Western blot analysis of Sf FKBP46: Sf9 cells were infected with wild type or vp35Δ and harvested 24–46 h after infection. The cells were lysed as above and the cell lysates were centrifuged at 800 g for 15 min and the nuclear pellets were collected and then suspended in SDS-sample buffer. The nuclear proteins were fractionated by SDS-PAGE, electroblotted onto a PVDF membrane and detected by Western blotting using a rabbit polyclonal antibody raised against Sf9 FKBP46 (Alnemri, E. S. et al., *J. Biol. Chem.* 1994, 269, 30828–30834). In some experiments, Sf9 cells were infected with recombinant baculovirus encoding Sf Caspase-1 and their proteins were analyzed as described above.

RESULTS AND DISCUSSION

Cloning of SF Caspase-1 proenzyme: Using a PCR approach developed recently in our lab to identify and clone novel members of the ASCP family from different species (Fernandes-Alnemri, T. et al., *Cancer Res.* 1995, 55, 2737–2742), several partial cDNAS were cloned from a unidirectional Sf9 cDNA library. Sequence analysis of some of these cDNAs resulted in identification of ~600 bp cDNA with extensive homology to human Mch3 and CPP32. This partial cDNA was used as a probe to clone a 2.4Kb cDNA that encodes a 299-amino acid protein, shown in FIG. 1A and SEQ ID NO:2, named Sf Caspase-1 proenzyme (Sf proCaspase-1), with a predicted molecular mass of ~35 kDa. FIG. 1A shows the Predicted amino acid sequence of Sf proCaspase-1 including the cleavage sites which define the subunits of the mature protein. The active site pentapeptide QACQG is boxed. Cleavage sites after Asp28, Asp184 and Asp195 are indicated by vertical arrows. The N-termini of the two subunits (p19/p18 and p12) are indicated by horizontal arrows.

Sf proCaspase-1 belongs to the CED-3 subfamily of Aspartate-Specific Cysteine Proteases. As shown in FIG. 1B, sequence alignment of Sf proCaspase-1 with all known ASCPs revealed that it has homology to other ASCPs. FIG. 1B shows multiple sequence alignment of Sf Caspase-1 with all known human ASCPs and the nematode Ced-3 ASCP. Based on crystal structure of ICE, the lowercase letters underneath the sequences indicate residues that are involved in catalysis (c), binding the substrate-carboxylate of P1 Asp (b) or adjacent to the substrate P2–P4 amino acids (a). D/X indicates known and potential processing sites between the small and large subunits of ASCPs. The Roman numbers on the left indicate the three ASCP-subfamilies; the Ced-like subfamily (I), the ICE-like subfamily (II) and the Nedd2/Ich-1 subfamily (III). The starting residue of each sequence is numbered to the left of the sequence.

The highest homology observed was to the human downstream apoptotic effectors Mch3 (42% identity, 60% similarity) (Fernandes-Alnemri, T. et al., *Cancer Res.* 1995, 55, 6045–6052), CPP32 (38% identity, 57% similarity) (Fernandes-Alnemri, T. et al., *J. Biol. Chem.* 1994, 269, 30761–307564) and Mch2α (38% identity, 54% similarity) (Fernandes-Alnemri, T. et al., *Cancer Res.* 1995, 55, 2737–2742), followed by other family members. Additionally, Sf proCaspase-1 belongs to the Ced-3 subfamily which includes the proenzymes of Ced-3, CPP32, Mch3, Mch4, Mch5 and Mch6. Sf proCaspase-1 is also structurally similar to other ASCPs. A mature Sf Caspase-1 could be derived from the precursor proenzyme by cleavage at Asp195 to generate the two subunits, and Asp15 and Asp28 which would remove the prodomain. Interestingly, Sf Caspase-1 has a QACQG active site pentapeptide, identical to that of Mch4 and Mch5.

Based on ICE and CPP32 crystal structures (Rotonda, J. et al., *Nature structural Biol.* 1996, 3, 619–625 and references therein), the Sf Caspase-1 residues corresponding to those that are involved in catalysis (His237, Gly238 and Cys285) and binding the carboxylate side chain of the substrate P1 aspartate (Arg179, Gln283, Arg341 and Ser347), are all conserved. The nonconserved residues that might participate in binding the substrate P2-P4 residues may determine the substrate specificity of Sf Caspase-1.

Expression, purification and microsequencing of Sf Caspase-1. To determine the enzymatic activity and primary structure of Sf-Caspase-1 and the exact autocatalytic processing sites in its proenzyme, it was expressed in bacteria, purified and microsequenced. This is because bacteria do not contain any ASCP activity and mutant Cys to Ala active site ASCPs are not autoprocessed in bacteria. Expression of Sf proCaspase-1 containing N-terminal T7-tag and C-terminal His6-tag, produced soluble mature enzyme. FIG. 2A shows results from experiments in which Sf proCaspase-1 was expressed in *E. coli*, purified, analyzed by SDS-PAGE and Coomassie staining and then microsequenced. Lane M is molecular weight markers; lane 1, $Ni^{2+}$-affinity purified mature Sf Caspase-1 enzyme. As shown in FIG. 2A, purified mature Sf Caspase-1 migrates in SDS-gels as three bands of apparent molecular masses of 19, 18 and 13 kDa. The N-terminal amino acid sequence of p12 is, GSPSTSYR-IPVHADFLIAFS. The N-terminus of the 13 kDa band starts with G196 indicating that processing occurred after Asp195 of Sf proCaspase-1. The calculated molecular mass of this peptide excluding the C-terminal His6-tag is ~12 kDa. The N-termini of the 19 kDa and 18 kDa bands start with Ala29, indicating that processing occurred after Asp28 of Sf proCaspase-1. Processing at these residues removes a 4 kDa prodomain. Site directed mutagenesis of Asp184 and Asp195 revealed that the difference in size between the two polypeptides is due to processing at Asp184 in the case of the 18 kDa polypeptide and Asp195 in the case of the 19 kDa band.

Figure 2B:
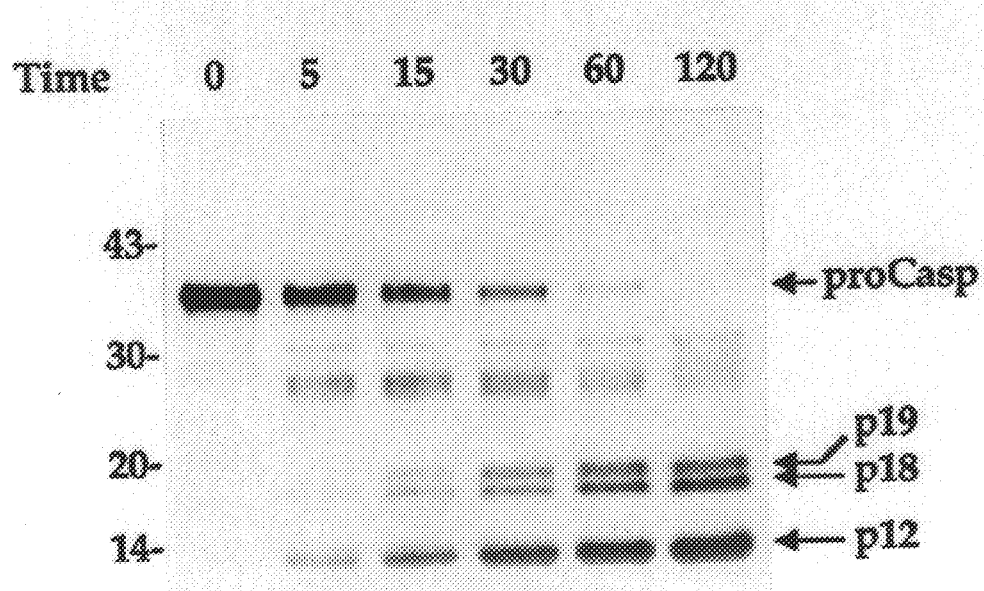

Similar results were also obtained after incubation of $^{35}$S-labeled Sf proCaspase-1 with mature recombinant Sf Caspase-1. FIG. 2B shows results from in vitro processing of Sf proCaspase-1 by mature recombinant Sf Caspase-1 enzyme. [$^{35}$S] methionine-labeled Sf proCaspase-1 was incubated with pure mature Sf Caspase-1 (25 ng) for the indicated times (min) at 37° C. The reaction products were then analyzed by Tricine-SDS-PAGE and autoradiography. Full length Sf proCaspase-1 and the cleavage products are indicated. Sf Caspase-1 was able to process its proenzyme in a time dependent fashion to generate the p19, p18 and p12 species.

Figure 2C:
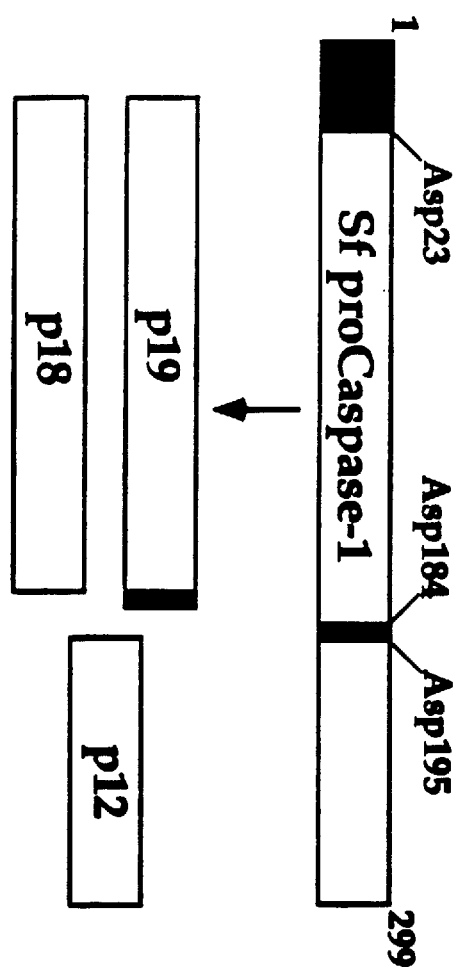

Based on these data, Sf proCaspase-1 can autoprocess after Asp28, Asp184 and Asp195 to generate the two subunits (p19/p18, large subunit and p12, small subunit) of mature Sf Caspase-1 enzyme. FIG. 2C shows a schematic diagram illustrating autoprocessing of Sf proCaspase-1. Sf ProCaspase-1 is autocatalytically processed at Asp195 and Asp28 to generate the mature p12/p19 enzyme complex. Additional processing also occurs at Asp184 to generate a mature p12/p18 enzyme complex.

p35 is a substrate and a potent inhibitor of Sf Caspase-1. Sf9 insect cells respond to baculovirus infection by activating a novel ASCP to initiate apoptosis (Bertin, J. et al., *J. Virol.* 1996, 70, 6251–6259). This process is counteracted by expression of the baculovirus encoded protein p35 which is a substrate for, and a potent inhibitor of members of the ASCP family (Bump, N.J. et al., *Science* 1995, 269, 1885–1888 and Xue, D et al., *Nature* 1995, 377, 248–251).

Figure 3A:
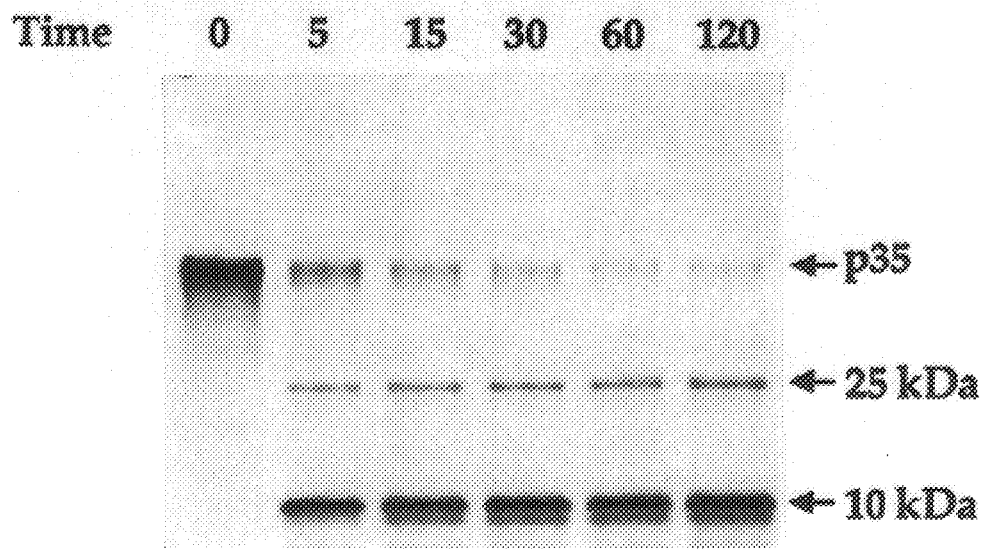
FIGS. 3A, 3B and 3C show data from experiments evaluating cleavage of p35 by Sf Caspase-1, CPP32 and Mch3.

To determine whether p35 is a substrate for Sf Caspase-1, purified recombinant Sf Caspase-1 was incubated with $^{35}$S-labeled p35 for various times. In FIG. 3A, [$^{35}$S] methionine-labeled p35 was incubated with pure mature Sf Caspase-1 (25 ng) for the indicated times (min) at 37° C. The reaction products were then analyzed by Tricine-SDS-PAGE and autoradiography. The full length p35 and the 25 kDa and 10 kDa cleavage products are indicated. The 25 kDa product is less radioactive because of lower methionine content.

Figure 3B:
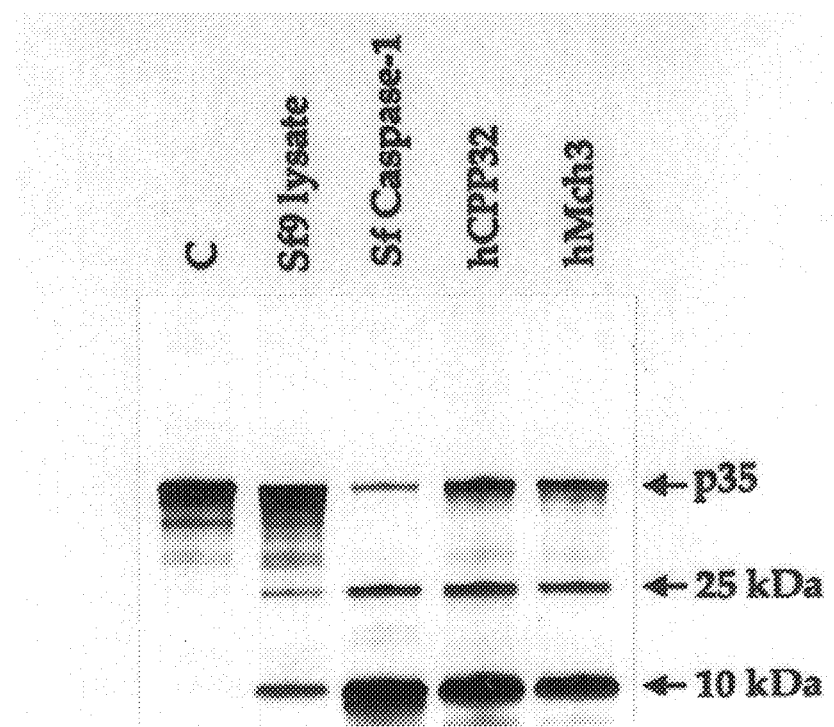

Identical results were also obtained with apoptotic extract from p35 null mutant virus-infected Sf9 cells, and recombinant human CPP32 and Mch3. FIG. 3B shows these results. In these experiments, [$^{35}$S] methionine-labeled p35 was incubated with buffer (lane 1), apoptotic extract from vp35Δ baculovirus-infected Sf9 cells (lane 2), Sf Caspase-1 (lane 3), recombinant hCPP32 (lane 4) or recombinant hMch3 (lane 5). As in FIG. 3A, the reaction products were then analyzed by Tricine-SDS-PAGE and autoradiography. The full length p35 and the 25 kDa and 10 kDa cleavage products are indicated. The 25 kDa product is less radioactive because of lower methionine content.

Figure 3C:
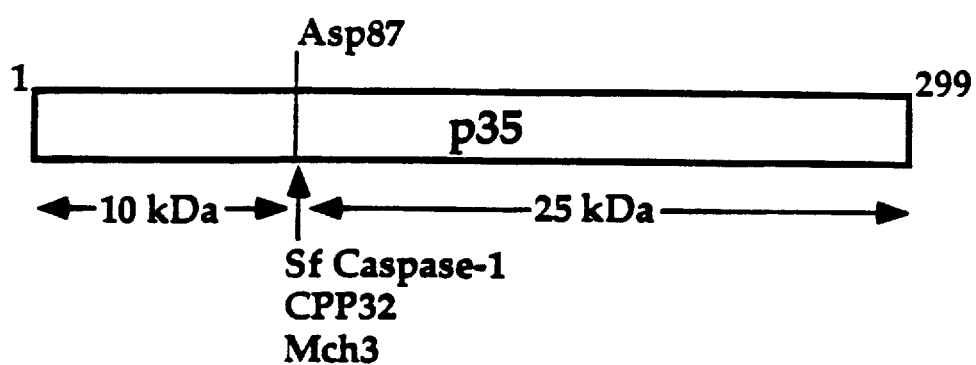

These experiments generated the expected 10 and 25 kDa fragments, indicative of cleavage at Asp87. FIG. 3C shows a schematic diagram illustrating the site of cleavage and the expected cleavage products of baculovirus p35 after interaction with Sf Caspase-1, CPP32 or Mch3.

Figure 4:
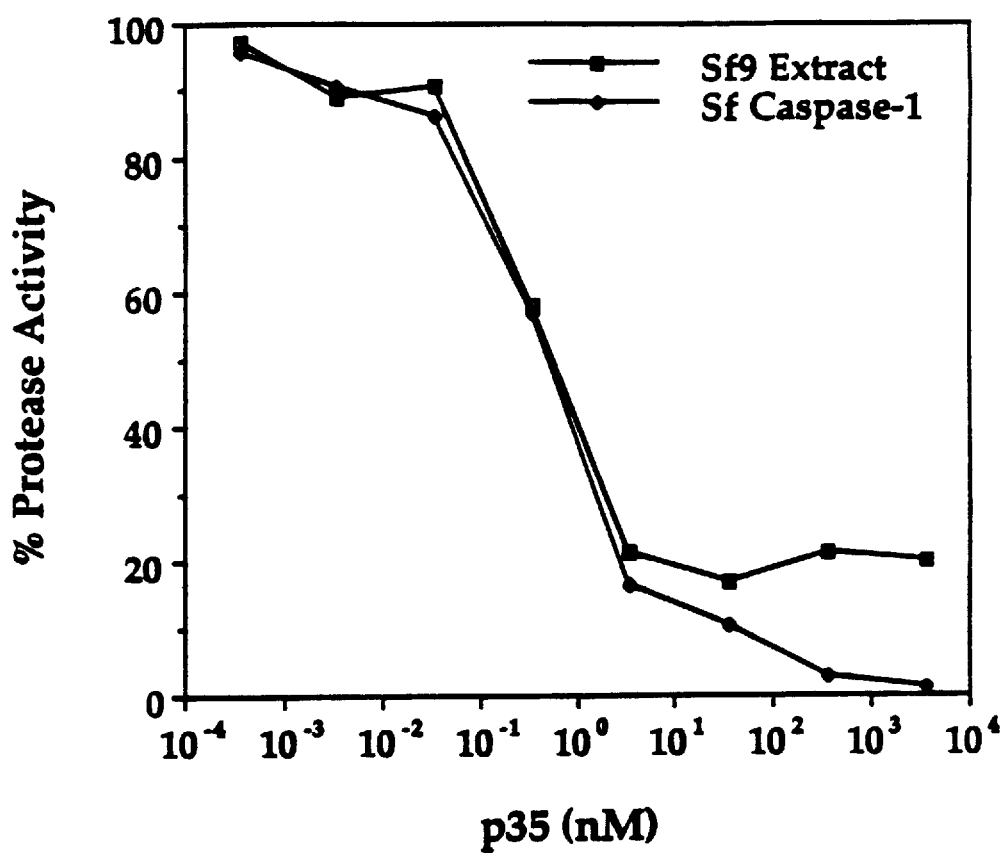
FIG. 4 shows data from experiments evaluating the inhibition of Sf Caspase-1 by recombinant p35.

Sf Caspase-1 was potently inhibited by purified recombinant p35 in a dose dependent manner (IC50~0.5 nM). FIG. 4 shows data from experiments evaluating the inhibition of Sf Caspase-1 by recombinant p35. Equivalent protease activity of recombinant Sf Caspase-1 or apoptotic lysate from vp35Δ baculovirus-infected Sf9 cells were incubated with the indicated concentrations of recombinant p35 and then assayed for protease activity using the tetrapeptide substrate DEVD-AMC. The enzymatic activities were expressed as a percentage of protease activity in the absence of p35. The endogenous protease activity in Sf9 apoptotic extract was also potently inhibited by p35 (IC50~0.5 nM) and exhibited a similar dose dependency. Unlike recombinant Sf Caspase-1, the protease activity in the Sf9 apoptotic extract was not completely inhibited by high concentrations of p35. This suggests that this extract contains an additional protease activity distinct from Sf Caspase-1 which is not sensitive to p35. This activity could be another novel ASCP that is activated by viral infection. The poxvirus CrmA which is a potent inhibitor of ICE, had very little effect on the activity of recombinant Sf Caspase-1 or Sf9 apoptotic extract under the same conditions. These results clearly establish that Sf Caspase-1 is the target of baculovirus p35 during viral infection of *S. frugiperda* insect cells.

The nuclear Sf FKBP46 is a target of Sf Caspase-1 in baculovirus-induced apoptosis. An Sf9 nuclear immunophilin named FKBP46 has been identified and cloned (Alnemri, E. S. et al., *J. Biol. Chem.* 1994, 269, 30828–30834 and U.S. Provisional Application No. 60/007,163 which is incorporated herein by reference). FKBP46 contains two N-terminal acidic domains with uninterrupted stretches of polyglutamic/aspartic acid residues. Because of the high content of Asp residues in these domains we decided to test whether FKBP46 is a target of Sf Caspase-1 in apoptosis. Sf9 cells were infected with wild type (WT) baculovirus (encodes p35) or p35 null mutant (vp35Δ) baculovirus and harvested 24 h after infection. Western blot analysis revealed that FKBP46 is cleaved to a ~25 kDa fragment in Sf9 cells infected with vp35Δ but not with wild type virus.

Figure 5:
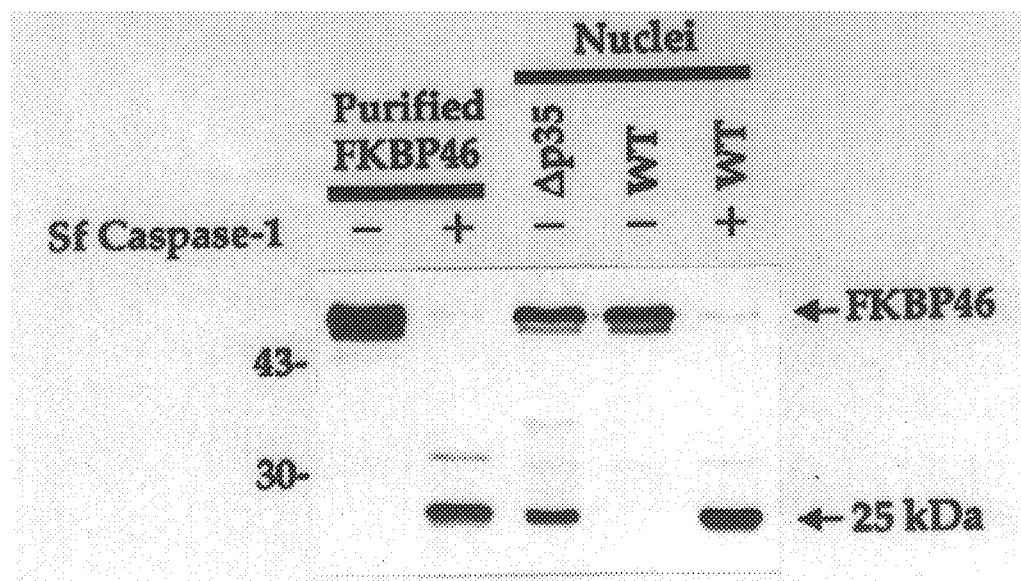
FIG. 5 shows data from experiments evaluating cleavage of the Sf nuclear immunophilin FKBP46 by Sf Caspase-1 and during vp35Δ baculovirus-induced apoptosis.

FIG. 5 shows data from experiments evaluating cleavage of the Sf nuclear immunophilin FKBP46 by Sf Caspase-1 and during vp35Δ baculovirus-induced apoptosis. Purified recombinant Sf FKBP46 (lanes 1 and 2) or nuclei from wild type virus infected Sf9 cells (24 h post-infection, lanes 4 and 5) were incubated with (+) or without (−) recombinant Sf Caspase-1 for 1 h at 37° C. and then analyzed by SDS-PAGE and immunoblotting with an FKBP46-specific polyclonal antibody. Nuclei from vp35Δ baculovirus-infected Sf9 cells (Δp35, lane 3) were isolated and directly analyzed by SDS-PAGE and immunoblotting. Full length and 30 kDa cleavage product of FKBP46 are indicated.

Since cells infected with vp35Δ virus but not wild type virus undergo rapid apoptosis as a result of activation of Sf Caspase-1, it is most likely that Sf Caspase-1 is the enzyme responsible for cleaving FKBP46. This was supported by our observations that incubation of recombinant Sf Caspase-1 with purified recombinant FKBP46 or Sf9 nuclei yielded the same ~25 kDa cleavage product (lanes 2 and 5).

Figure 6A:
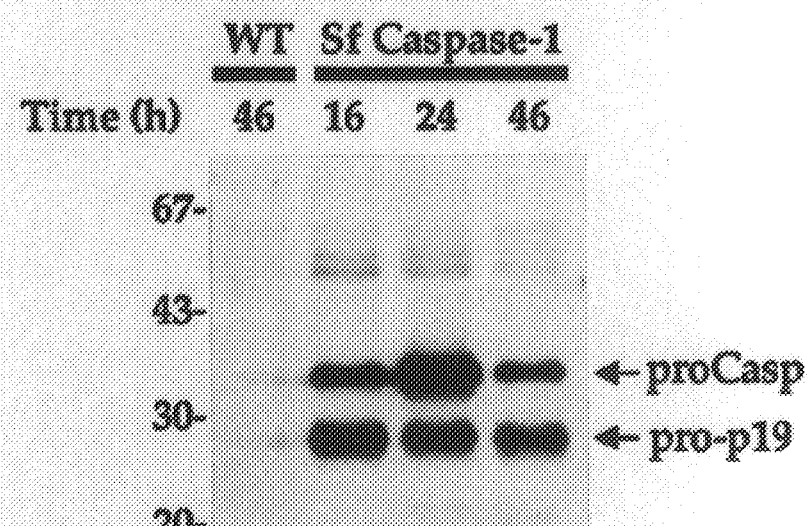
FIGS. 6A, 6B, 6C and 6D shows data from experiments evaluating overexpression of Sf proCaspase-1 in SF9 cells results in its activation, cleavage of FKBP46 and DNA cleavage.
Figure 6B:
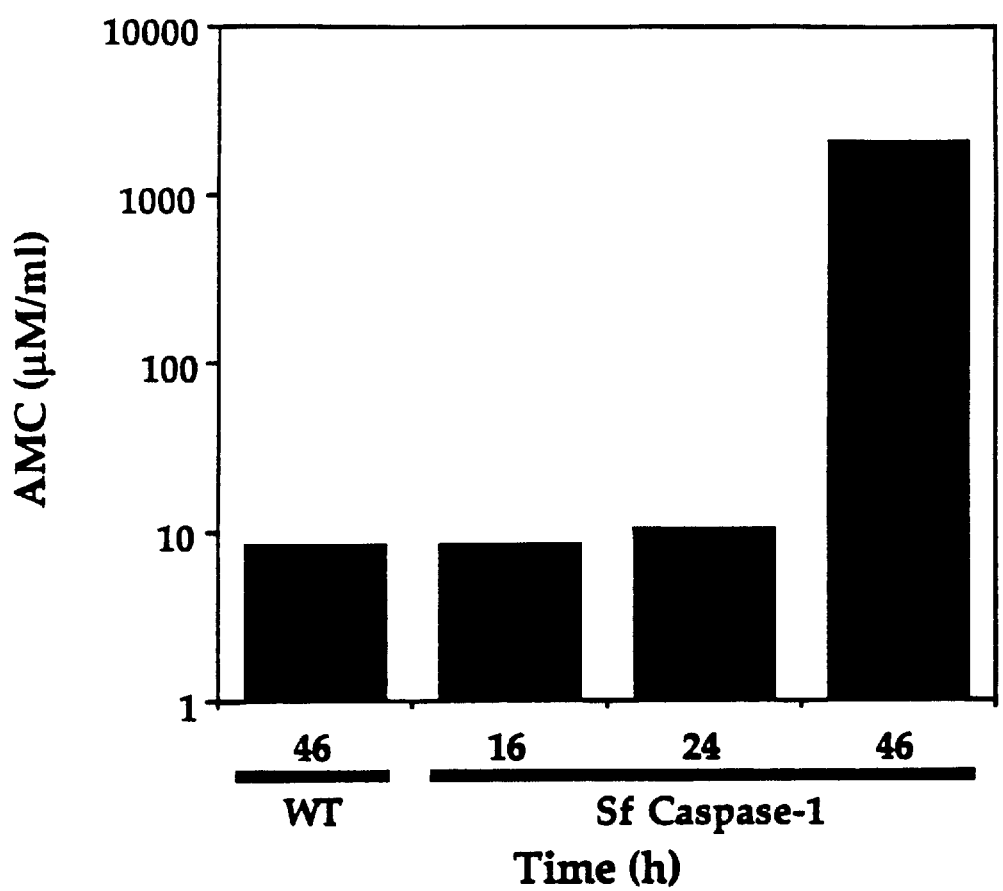
Figure 6C:
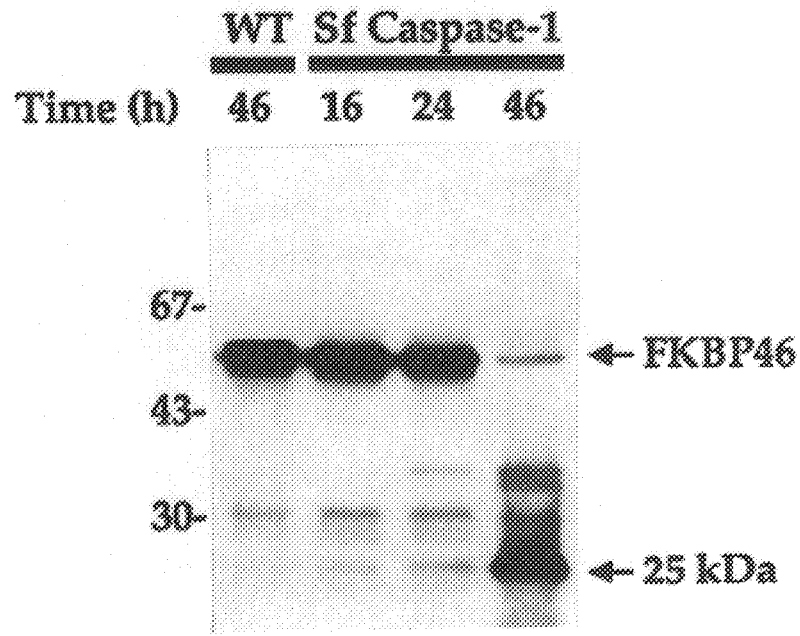
Figure 6D:
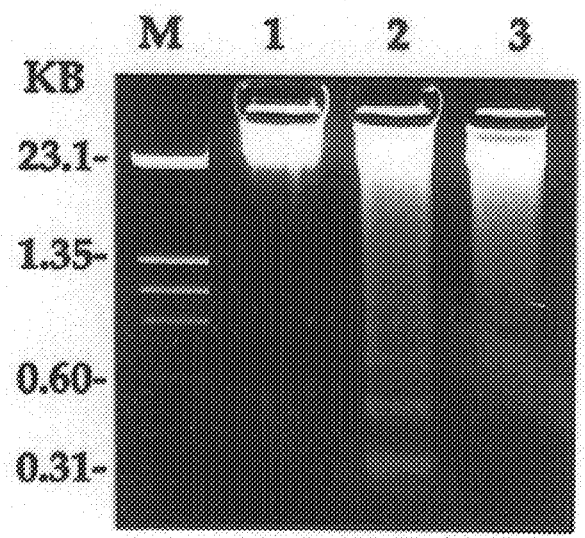

FIGS. 6A, 6B, 6C and 6D shows data from experiments evaluating overexpression of Sf proCaspase-1 in SF9 cells results in its activation, cleavage of FKBP46 and DNA cleavage. Sf9 cells were infected with recombinant baculovirus encoding T7-tagged Sf proCaspase-1 under the polyhedrin promoter or wild type baculovirus. At the indicated times shown in FIGS. 6A, 6B and 6C, the cells were harvested, fractionated into cytosolic and nuclear fractions and the cytosolic fractions were analyzed by Western blotting with a T7-antibody (FIG. 6A) or by enzymatic assay with the DEVD-AMC peptide substrate (FIG. 6B). The nuclear fractions were analyzed by Western blotting with the FKBP46 antibody (FIG. 6C). The activity in the Sf Caspase-1 virus lysates was expressed relative to the activity in the wild type virus lysate. FIG. 6D shows data from experiments evaluating induction of DNA cleavage by overexpressed Sf Caspase-1. Total DNA was isolated from Sf9 cells infected with wild type baculovirus (negative control, lane 1) or recombinant baculoviruses encoding ProICEλ (positive control, lane 2) or Sf proCaspase-1 (lane 3) and then analyzed by 1.8% agarose-gel electrophoresis.

These data demonstrate that overexpression of Sf proCaspase-1 in Sf9 cells resulted in its processing as determined by immunostaining with T7 antibody (FIG. 6A) and generation of maximal Sf Caspase-1 activity at 46 h post infection (FIG. 6B). The lower Sf Caspase-1 activity observed at 16–24 h post infection (FIG. 6B) might be due to p35 inhibition which is stoichiometric. In addition, the lower T7-immunostaining observed at 46 h post infection is due to removal of the T7-tagged prodomain by the high Sf Caspase-1 activity. Maximal cleavage of FKBP46 (FIG. 6C) and induction of apoptosis with characteristic internucleosomal DNA cleavage (FIG. 6D) were observed at 46 h postinfection.

In conclusion, two novel components of the apoptotic machinery of the insect *Spodoptera frugiperda,* the host of the baculovirus *Autographa californica* have bee identified and characterized. The death effector component is an ASCP named Sf-Caspase-1, highly related to the mammalian apoptotic effectors Mch3, CPP32 and Mch2α. Mature Sf Caspase-1 can cleave the baculovirus antiapoptotic protein p35, is potently inhibited by p35 and exhibits similar p35-inhibitory profile as the endogenous Sf9 protease present in Sf9 apoptotic extracts. Thus Sf Caspase-1 is most likely the target of baculovirus p35. The second component is a death substrate known as FKBP46, which is an Sf9 nuclear DNA binding immunophilin. We demonstrated that FKBP46 is cleaved specifically during vp35α baculovirus-induced apoptosis of Sf9 cells and by the death effector component Sf Caspase-1. Because the basic apoptosis program has been highly conserved during evolution, the identification of these two components should facilitate the efforts to elucidate the molecular mechanism and the physiological significance of apoptosis in diverse organisms ranging from insects to mammals.

We claim:

1. An isolated nucleic acid molecule that comprises a nucleic acid sequence that encodes the protein having the amino acid sequence of SEO ID NO:2.

2. An isolated nucleic acid molecule consisting of SEQ ID NO:1 or a fragment thereof having at least 18 nucleotides.

3. The nucleic acid molecule of claim 2 consisting of SEQ ID NO:1.

4. A recombinant expression vector comprising the nucleic acid molecule of claim 3.

5. A host cell comprising the recombinant expression vector of claim 4.

6. The nucleic acid molecule of claim 2 consisting of a fragment of SEQ ID NO:1 having at least 18 nucleotides.

7. The nucleic acid molecule of claim 2 consisting of a fragment of SEQ ID NO:1 having at least 150 nucleotides.

8. The nucleic acid molecule of claim 2 consisting of a fragment of SEQ ID NO:1 having up to 50 nucleotides.

9. An oligonucleotide molecule of claim 2 comprising a nucleotide sequence complimentary to a nucleotide sequence of at least 18 nucleotides of SEQ ID NO:1.

10. The oligonucleotide molecule of claim 9 wherein said oligonucleotide molecule comprises a nucleotide sequence complimentary to a nucleotide sequence of up to 50 nucleotides of SEQ ID NO:1.

11. The oligonucleotide molecule of claim 9 wherein said oligonucleotide molecule comprises a nucleotide sequence complimentary to a nucleotide sequence of up to 40 nucleotides of SEQ ID NO:1.

12. An oligonucleotide molecule of claim 9 consisting of a nucleotide sequence complimentary to a nucleotide sequence of at least 150 nucleotides of SEQ ID NO:1.

13. The oligonucleotide molecule of claim 9 consisting of a nucleotide sequence complimentary to a nucleotide sequence of at least 18–28 nucleotides of SEQ ID NO:1.

* * * * *